United States Patent [19]

Butterfield

[11] Patent Number: 4,713,056
[45] Date of Patent: Dec. 15, 1987

[54] NON-REUSABLE HYPODERMIC SYRINGE

[75] Inventor: Ida M. Butterfield, Santa Maria, Calif.

[73] Assignee: Butterfield Group, Santa Maria, Calif.

[21] Appl. No.: 877,288

[22] Filed: Jun. 23, 1986

[51] Int. Cl.⁴ .............................................. A61M 5/00
[52] U.S. Cl. ................................................. 604/110
[58] Field of Search ................. 604/110, 111, 88, 187, 604/218

[56] References Cited

U.S. PATENT DOCUMENTS

| | | | |
|---|---|---|---|
| 4,031,892 | 6/1977 | Hurschman | 604/88 X |
| 4,233,975 | 11/1980 | Yerman | 604/110 |
| 4,252,118 | 2/1981 | Richard et al. | 604/110 |
| 4,391,272 | 7/1983 | Staempfli | 604/110 |

Primary Examiner—John D. Yasko
Attorney, Agent, or Firm—Daniel C. McKown

[57] ABSTRACT

A hypodermic syringe is rendered non-reusable by means of a special latching device that prevents a portion of the piston from being retracted and that causes that portion to seal off the syringe at the end of it to which the needle is attached. The latching device is lodged into a groove recessed into the cylindrical inner surface of the syringe like a snap ring, and includes elastically deflectable fingers that extend axially and slightly inwardly radially in the direction toward the needle, so that the tips of the fingers extend into the path of the piston, are elastically deflected aside by the piston and spring inward again after the piston has passed, thereby blocking movement of the piston in the opposite direction and rendering the syringe non-reusable.

5 Claims, 4 Drawing Figures

NON-REUSABLE HYPODERMIC SYRINGE

BACKGROUND OF THE INVENTION

1. Field of the Invention

The present invention is in the field of hypodermic syringes and more specifically relates to a type of hypodermic syringe that can be supplied in an empty condition, into which a fluid can be aspirated, and which can easily be rendered non-reusable after the first use.

2. The Prior Art

In a number of foreign countries mass immunization programs are being conducted to control certain diseases endemic to those countries. While this is highly desirable, the syringes used remain reusable after their intended use. Repeated use of these hypodermic needles is one of the major causes of the spread of more than 15 diseases including AIDS and hepatitis.

What is desperately needed is a fool-proof technique for rendering the syringes used for immunization non-reusable.

In U.S. Pat. No. 4,391,272 issued July 5, 1983 to Staempfli and in U.S. Pat. No. 4,233,975 issued Nov. 18, 1980 to Yerman there are shown various embodiments of syringes in which, typically, a barb on the plunger engages a groove in the cylindrical wall of the syringe to prevent the plunger from being retracted.

In these patents, the drive rod pulls out of the plunger if an attempt is made to retract the plunger after it has been placed in the latched position. This aspect raises doubts regarding the possibility of aspirating fluid into these syringes. Because the fluid being aspirated cannot flow rapidly through the small bore of the needle, any attempt to retract the plunger rapidly will be met by a substantial resistive force. This force might possibly dislodge the drive member from the plunger. Also, the drive rod could be glued back in place.

The present invention permits rapid aspiration of fluid into the syringe, and provides a different mechanism for latching the plunger after all of the contents of the syringe have been expressed, thereby rendering the syringe non-reusable.

In U.S. Pat. No. 3,941,129 Pleznac discloses that a stopper located in the bore of a syringe adjacent but not connected to the drive piston can be used to give an unalterable visual alert if the drive piston has been advanced in the cylinder prior to the intended use; i.e., if the syringe has been tampered with. The present invention improves on this syringe by providing means to render it non-reusable.

SUMMARY OF THE INVENTION

In accordance with the present invention, the drive rod does not pull out of the plunger, but instead extends through the piston and is shaped like a nail with a circular head. It is this disk-like metallic header that is caught and retained by the latching mechanism.

In accordance with the present invention, there is provided a novel latching structure which is emplaced in a groove in the cylindrical wall of the syringe. The elasticity of the piece causes it to expand within the groove, thereby preventing it from coming out of the groove. The device includes fingers that are angled radially inwardly toward the front of the syringe, and these fingers prevent retraction of the disk-like head of the piston.

In the syringes described in the aforementioned patents, the piston was made of a relatively soft material such as a plastic. It is well known that some plastics deform under prolonged force and that some plastics are affected by heating.

In contrast, the syringe of the present invention is more robust because the parts that form the latching mechanism can all be made of metal.

The novel features that are believed to be characteristic of the invention will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 3 is a fractional side view in cross-section showing an alternative embodiment of the hypodermic syringe of the present invention; and, FIG. 4 is a fractional side view in cross-section showing a hypodermic syringe in accordance with an alternative embodiment that provides a visual alert if the syringe has been tampered with.

DETAILED DESCRIPTION OF THE PREFERRED EMBODIMENT

Figure 1:
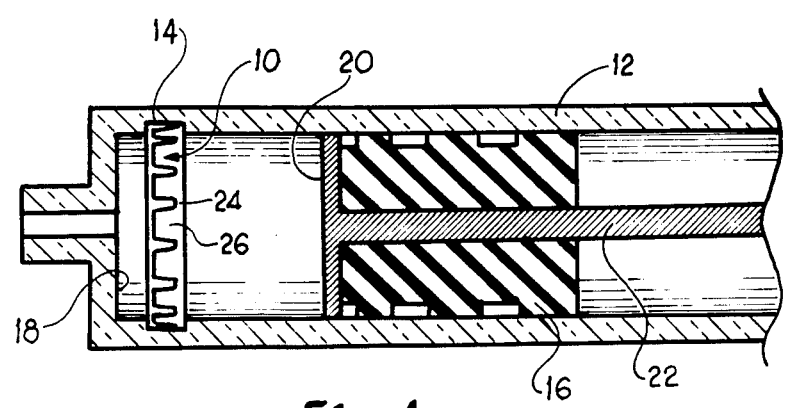
FIG. 1 is a fractional side view in cross-section showing a hypodermic syringe in accordance with the preferred embodiment.

FIG. 1 shows a preferred embodiment of the invention in a side cross-sectional view. A hypodermic needle would be attached to the left end of the syringe.

The syringe includes a tubular member 12 in which a drive piston 16 may be moved axially by the user by pushing or pulling on the rod 22. The rod 22 terminates in a disk-like head 20 which is very slightly undersized with respect to the bore of the tubular member 12, so that it moves with a loose sliding fit. The drive piston 16 is bonded to the rod 22 and its head 20.

The tubular member 12 also includes an internal groove 14 that is located a short distance from the end 18 of the chamber. That distance must be larger than the thickness of the head 20, and in a preferred embodiment the distance is approximately twice the thickness of the head 20. A latch ring 10 resides in the groove 14. The latch ring 10 is shown in greater detail in FIG. 2.

Figure 2:
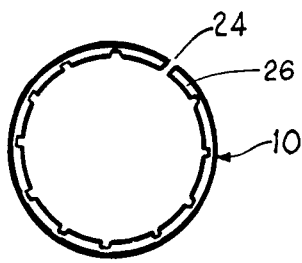
FIG. 2 is a plan view showing a latching ring used in the preferred embodiment of FIG. 1.

In its free state, the diameter of the latch ring 10 is greater than the diameter of the groove 14, and the ring must be compressed to allow it to pass down the length of the tubular member 12 so that it can be seated in the groove 14. As shown in FIG. 2, the latch ring 10 is not completely closed, but instead includes the gap 24 which permits it to be compressed for installation. It installs like a snap ring. From the latch ring 10 a number of fingers, of which the finger 26 is typical, extend predominantly axially, as best seen in FIG. 1. The fingers also extend radially inwardly as they extend toward the front of the syringe.

When the latch ring 10 has been seated in the groove 14, the tips of the fingers extend slightly into the cylindrical space defined by the cylindrical walls of the tubular member 12. That is, the tips of the fingers extend into the path of the disk-like head 20. The fingers are pushed into the groove 14 by passage of the head 20, and when the latter has cleared the tips of the fingers, the finger tips spring back to their normal position to prevent retraction of the head 20. Some of the resilience of the finger tips is derived from the flexing of the fingers themselves, and some of the resilience is due to rolling of the latch ring about its circular axis. The harder the rod 22 is pulled to the right, the more tightly the latch ring 10 is forced against the groove 14.

In the preferred embodiment, the tubular member is made of glass, and the head 20 as well as the latch ring 10 are made of metal. This results in an extremely robust structure, and one which is unaffected by heating.

In an alternative embodiment, the tubular member 12, the head 20 and the latch ring 10 are all formed of the same composition of plastic. This alternative embodiment has the advantage that the only materials coming into contact with the fluid are those same materials which would be in contact with the fluid if the invention were not used at all. Also, if the head 20 is made of plastic, it can sealingly engage the inside wall of the syringe, and the drive piston 16 can be omitted.

Figure 3:
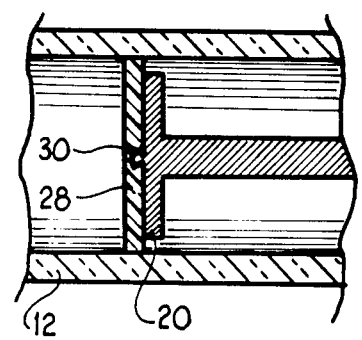

FIG. 3 shows another alternative embodiment of the present invention, which embodiment is identical to that of FIG. 1 except that a disk-like seal 28 is removably attached to the head 20 by one or more knob-like projections 30. The seal 28 sealingly engages the cylindrical inner walls of the tubular member 12.

When the rod 22 is pushed as far as possible to the left, the seal 28 passes the inwardly projecting fingers 26 and is retained by them. If, thereafter, the rod 22 is pulled to the right, the seal 28 is retained at the left hand end of the chamber because the knob 30 is pulled free of the seal 28. In its position at the end of the chamber, the seal 28 prevents the flow of fluid through the needle in any direction. Also, the head 20 because of its reduced diameter does not sealingly engage the cylindrical inner wall of the tubular member 12, and therefore is useless.

The seal 28 must be attached to the head 20 securely enough to prevent it from pulling loose when the rod 22 is moved to the right to aspirate fluid. On the other hand, the nexis must break at a force considerably less than the force required to pull the seal to the right against the latching action of the fingers 26. In this embodiment, the seal 28 is preferably made of a plastic material.

In other variations of the embodiment of FIG. 3, the projections 30 may have other shapes. In another variation, the seal 28 is bonded to the head 20 by an adhesive. In still another variation, the seal 28 and the head 20 are interconnected by a frangible member.

Figure 4:
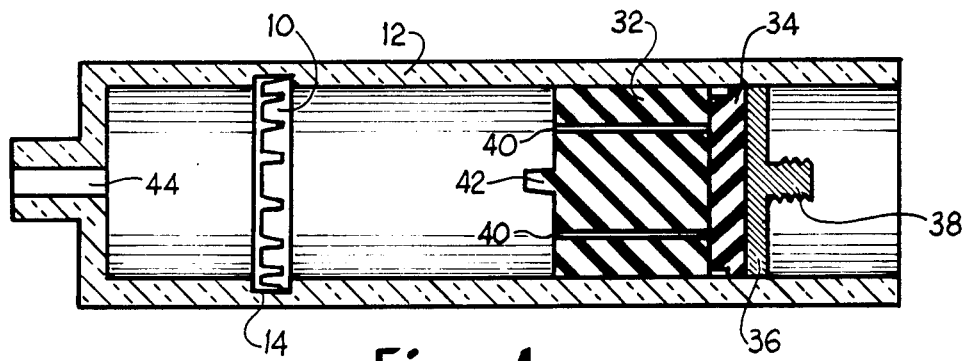

FIG. 4 shows another embodiment of the present invention. This embodiment provides a visual alert to signal that the piston has been advanced into the cylinder. The visual alert is provided by the stopper 32 which is not connected to the piston 34. The piston 34 is bonded to the disk-like head 36 which provides rigidity and has a threaded projection 38 to which a drive rod can be attached. Both the stopper 32 and the piston 34 sealingly engage the cylindrical inside wall of the tubular member 12.

The stopper 32 includes two passages which extend through it in the axial direction to permit fluid to be aspirated. The stopper 32 further includes a projection 42 that has a frusto-conical shape and is sized to fit into the passage 44 to seal it when the stopper 32 has been pushed leftward to the end of the cylindrical chamber. The tubular member 12 is provided with a groove 14 in which the latch ring 10 (shown also in FIG. 2) resides.

The latch ring 10 prevents the stopper 32 from being withdrawn even if a wire is forced through the passage 44 in an attempt to dislodge the stopper. In a preferred mode, the fingers 26 of the latch ring 10 are so positioned axially that the stopper 32 is retained under a slight compression, so as to assure that the projection 42 will tightly seal the passage 44.

Thus, provision of the projection 42 to the stopper 32 permits the stopper to serve dual purposes; it gives visual indication of the fact that the piston 34 has been advanced into the cylinder, and secondly, it serves to seal off the passage 44.

The advantages of the embodiment shown in FIG. 4 are that the stopper 32 gives a visual alert in event the fluid with which the syringer was orginally filled has been partially expressed and/or replaced. The passages 40 permit aspiration of additional fluid into the syringe as is sometimes required when certain fluids must be mixed immediately before injection. Finally, the projection 42 on the stopper, in combination with the latch ring 10 renders the syringe non-reusable.

Thus, there has been described several embodiments and variations of the present invention, and other variations will be apparent to workers in the art. All of these variations and embodiments are considered to be within the scope of the present invention which is limited only by the following claims.

What is claimed is:

1. A non-reusable hypodermic syringe characterized in that it is extremely robust, and comprising:
    a hollow cylindrical tubular member closed at a first end except for an axial passage, having a cylindrical inside wall, and including portions defining an internal circumferential groove located adjacent but spaced axially from said first end;
    a drive rod extending axially in said tubular member;
    a piston head permanently attached to the end of said drive rod nearest the first end, slidable axially within said tubular member, and substantially rigid;
    a latch ring consisting of a generally ring-shaped unitary structure, residing in said groove, and including resilient fingers that all extend toward said first end and slightly radially inwardly into the cylindrical space defined within the cylindrical inside wall of said tubular member, the resiliency of said fingers permitting them to deflect into said groove when said piston head is pushed toward said first end past said fingers, and then to spring back into the cylindrical space to catch against said piston head when the latter is pulled away from said first end, thereby preventing refilling of the syringe by preventing movement of said piston head away from said first end.

2. The non-reusable hypodermic syringe of claim 1 wherein said piston head, said drive rod, and said latch ring are each composed of a metal.

3. A non-reusable hypodermic syringe comprising:
    a hollow cylindrical tubular member closed at a first end except for the orifice of an axial passage, having a cylindrical inside wall, and including portions defining an internal circumferential groove located adjacent but spaced axially from the first end;
    a drive rod extending axially in said tubular member and including a head at the end of the drive rod nearest the first end;
    a seal attached to the head of said drive rod, sealingly engaging the cylindrical inside wall, and slidable axially within said tubular member; and, a latch ring consisting of a generally ring-shaped unitary structure, residing in the groove in said tubular member, and including resilient fingers that all extend toward the first end and slightly radially inwardly into the cylindrical space defined within the cylindrical inside wall of said tubular member, the resiliency of the fingers permitting them to deflect into the groove when said seal is pushed toward the first end past the fingers, and then to spring back into the cylindrical space defined by the cylindrical inside wall, catching against said seal and preventing it from being moved away from the first end, and holding said seal against the first end, in which position said seal seals the orifice of the axial passage preventing any flow of fluid between the axial passage and the space within said tubular member, thereby rendering the syringe non-reusable.

4. The non-reusable hypodermic syringe of claim 3 wherein said seal is removably attached to the head of said drive rod and is detachable by sufficient force, whereby when said drive rod is pulled with sufficient force away from the first end, said seal detaches from said drive rod rendering said drive rod useless for aspirating and expressing fluid, and leaving the orifice sealed by said seal, whereby said syringe is rendered non-reusable.

5. A hypodermic syringe characterized in that it is non-reusable, it permits a fluid to be aspirated, and it gives an unalterable visual alert if it has been tampered with prior to use, comprising:

a hollow cylindrical tubular member closed at a first end except for the orifice of an axial passage, having a cylindrical inside wall, and including portions defining an internal circumferential groove located adjacent but spaced axially from the first end;

a piston sealingly engaging the cylindrical inside wall and slidable axially within said tubular member;

a stopper located within said tubular member between the first end and said piston, initially in contact with said piston but not connected to it, sealingly engaging the cylindrical inside wall, slidable axially within said tubular member, and including portions for sealing the orifice of the axial passage when said stopper has been pushed to the first end, said stopper further including portions that define a passage that extends axially all the way through said stopper to permit fluid to be aspirated without moving said stopper, whereby movement of said piston toward the first end pushes said stopper ahead of it to an altered position, and thereafter, movement of said piston in the opposite direction does not change the altered position of said stopper so that the displacement of said stopper from its initial position serves as a visual alert that the syringe has been tampered with; and, a latch ring consisting of a generally ring-shaped unitary structure, residing in the groove in said tubular member, and including resilient fingers that all extend toward the first end and slightly radially inwardly into the cylindrical space defined within the cylindrical inside walls of said tubular member, the resiliency of the fingers permitting them to deflect into the groove when said stopper is pushed toward the first end past the fingers, and then to spring back into the cylindrical space defined by the cylindrical inside wall to catch against said stopper to prevent it from being moved away from the first end, and holding said stopper against the first end, in which position said stopper seals the orifice of the axial passage preventing any flow of fluid between the axial passage and the space within said tubular member, thereby rendering the syringe non-reusable.

* * * * *